(12) United States Patent
Lai

(10) Patent No.: US 6,204,412 B1
(45) Date of Patent: Mar. 20, 2001

(54) METHOD OF MANUFACTURING ALKYLATED DIPHENYLAMINE COMPOSITIONS AND PRODUCTS THEREOF

(75) Inventor: John T. Lai, Broadview Heights, OH (US)

(73) Assignee: The B. F. Goodrich Company, Brecksville, OH (US)

( * ) Notice: Subject to any disclaimer, the term of this patent is extended or adjusted under 35 U.S.C. 154(b) by 0 days.

(21) Appl. No.: 09/292,865

(22) Filed: Apr. 16, 1999

(51) Int. Cl.$^7$ .................................................. C07C 209/68
(52) U.S. Cl. ............................................ 564/409; 564/433
(58) Field of Search ...................................... 564/409, 433

(56) References Cited

U.S. PATENT DOCUMENTS

| | | |
|---|---|---|
| 2,943,112 | 6/1960 | Popoff et al. . |
| 3,452,056 | 6/1969 | Sundholm . |
| 3,655,559 | 4/1972 | Holt . |
| 4,824,601 | 4/1989 | Franklin . |
| 5,214,211 | 5/1993 | Kurek et al. . |
| 5,672,752 | 9/1997 | Lai et al. . |
| 5,750,787 * | 5/1998 | Lai et al. .............................. 564/409 |

FOREIGN PATENT DOCUMENTS 0810200    12/1997   (EP) .

OTHER PUBLICATIONS

Journal of Catalysts, vol. 160, pp. 84–94, Jan. 1, 1996, Article No. 0126, Sandeep R. Chitnis et al., XP–002085239, "Alkylation of Diphenylamine With α–Methylstyrene and Diisobutylene Using Acid–Treated Clay Catalysts".

Pierre Laszlo, "Chemical Reactions on Clays", Science, vol. 235, No. 4795, pp. 1473–1477 (Mar. 20, 1987).

\* cited by examiner

*Primary Examiner*—Samel Barts
*Assistant Examiner*—Brian J. Davis
(74) *Attorney, Agent, or Firm*—Thoburn T. Dunlap; Valerie L. Calloway; Bruce E. Black

(57) ABSTRACT

A method of manufacturing an alkylated diphenylamine composition to generate an alkylated diphenylamine composition with relatively low amounts of unsubstituted diphenylamine, based on the total weight of substituted and unsubstituted diphenylamine in the alkylated diphenylamine composition. The method includes reaction of unsubstituted diphenylamine with at least two olefins. In at least some instances, the alkylated diphenylamine composition may be used, for example, as an antioxidant in a lubricating fluid or polymer composition.

18 Claims, No Drawings

METHOD OF MANUFACTURING ALKYLATED DIPHENYLAMINE COMPOSITIONS AND PRODUCTS THEREOF

FIELD OF THE INVENTION

This invention relates to methods of manufacturing alkylated diphenylamine compositions and the compositions formed thereby. In particular, the invention relates to methods of manufacturing alkylated diphenylamine compositions by reaction of unsubstituted diphenylamine with two or more olefins.

BACKGROUND OF THE INVENTION

Unsubstituted diphenylamine can be used as an antioxidant, but it tends to yellow. A number of alkylated diphenylamines have shown good antioxidant activity in, for example, lubricating oils and polymeric molding compositions. These alkylated diphenylamines are typically low in yellow coloring and are resistant to further yellowing.

Antioxidant compositions have been formed by alkylating unsubstituted diphenylamine to produce a mixture of alkylated diphenylamines. Suitable alkylated diphenylamine compositions for use as antioxidants are liquids at room temperature (for example, 25° C.) that contain no more than 3 wt. % unsubstituted diphenylamine, based on the total weight of substituted and unsubstituted diphenylamine in the alkylated diphenylamine composition.

Alkylation reactions of unsubstituted diphenylamine typically produce, among other reaction products, symmetrically disubstituted diphenylamines (e.g., dioctyldiphenylamine or dibutyldiphenylamine). Symmetrically disubstituted diphenylamines typically increase the melting point of the alkylated diphenylamine composition. In sufficient amounts (depending on the particular symmetrically disubstituted diphenylamine and the other components of the composition), the result is a solid alkylated diphenylamine composition rather than a liquid. For example, a composition with 25 wt. % or more dioctyldiphenylamine (based on the total weight of substituted and unsubstituted diphenylamine) is typically solid at room temperature. Thus, to obtain the desired liquid compositions with low amounts of unsubstituted diphenylamine, a balance must be found between forming symmetrically disubstituted diphenylamine and leaving unsubstituted diphenylamine in the composition.

The formation of alkylated diphenylamine compositions by reacting unsubstituted diphenylamine with diisobutylene is described in U.S. Pat. No. 5,750,787 and references cited therein. However, diisobutylene may not be sufficiently reactive to reduce the amount of unsubstituted diphenylamine in the alkylated diphenylamine composition to less than 3 wt. % in a suitable period of time and/or without increasing the amount of dioctyldiphenylamine in the alkylated diphenylamine composition above 25 wt. %, based on the total weight of substituted and unsubstituted diphenylamine in the alkylated diphenylamine composition.

A second olefin, which is more reactive with unsubstituted diphenylamine than diisobutylene under the reaction conditions, may be added to scavenge or reduce the amount of unsubstituted diphenylamine. Examples of such olefins include isobutylene, styrene, and α-methylstyrene. In conventional methods, the second olefin is added after the reaction of unsubstituted diphenylamine and diisobutylene is substantially complete or has proceeded to a particular point. According to the method described in U.S. Pat. No. 5,750,787, incorporated herein by reference, the desired alkylated diphenylamine composition is formed if the second olefin is added after the reaction between unsubstituted diphenylamine and diisobutylene has produced a reaction composition with less than 25 wt. % dioctyldiphenylamine, less than 25 wt. % unsubstituted diphenylamine, and greater than 50 wt. % monooctyldiphenylamine, based on the total weight of unsubstituted and substituted diphenylamine in the reaction composition.

The components of the alkylated diphenylamine compositions may affect other properties of the composition. For example, it is believed that both symmetric and asymmetrically disubstituted diphenylamines provide better color stability than monosubstituted diphenylamines when mixed with resins. Because symmetrically disubstituted diphenylamines increase the melting point of the composition and may result in the formation of solid, rather than liquid, compositions, the amount of symmetrically disubstituted diphenylamine(s) is typically limited. However, asymmetrically disubstituted diphenylamines, such as butyloctyldiphenylamine, have less effect on the melting point while typically providing the better color stability.

SUMMARY OF THE INVENTION

Generally, the present invention relates to the formation of dialkylated diphenylamine compositions. One embodiment is a method of manufacturing an alkylated diphenylamine composition. Unsubstituted diphenylamine and at least one compound selected from the group of diisobutylene and α-olefins having formula (I)

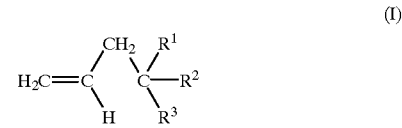

where $R^1$, $R^2$, and $R^3$ are functional groups that do not substantially interfere with alkylation of unsubstituted diphenylamine via the α-olefinic bond of the α-olefin, are combined in the presence of a clay catalyst to form a reactive composition. A second olefin composition is added to and reacted with the reactive composition. The resulting reaction product is an alkylated diphenylamine composition having no more than 3 wt. % unsubstituted diphenylamine, based on the total weight of substituted and unsubstituted diphenylamine in the alkylated diphenylamine composition.

Typically, at least a portion of the second olefin composition is added to the reactive composition prior to forming, in the reactive composition, at least 50 wt. % monoalkylated diphenylamine, based on the total weight of substituted and unsubstituted diphenylamine in the reactive composition at the time the addition of the second olefin composition is initiated. In some instances, at least a portion of the second olefin composition is added to the reactive composition within 30 minutes, and, in some cases, within 10 minutes, of beginning to combine the unsubstituted diphenylamine and diisobutylene or α-olefin of formula (I). The second olefin composition typically includes at least one second olefin that is more reactive (i.e., reacts more quickly) with unsubstituted diphenylamine than diisobutylene and/or α-olefins having formula (I) under the same reaction conditions.

The alkylated diphenylamine composition formed by this method may, in some embodiments, include no more than 25 wt. % dioctyldiphenylamine, at least 25 wt. % butyloctyldiphenylamine, and/or no more than 40 wt. % monosubstituted diphenylamines, based on the total weight of substituted and unsubstituted diphenylamine in the alkylated diphenylamine composition.

Another embodiment of the invention includes reacting unsubstituted diphenylamine, diisobutylene, and isobutylene in the presence of a clay catalyst to form an alkylated diphenylamine composition that includes at least 25 wt. % butyloctyldiphenylamine, no more than 3 wt. % unsubstituted diphenylamine, and no more than 25 wt. % dioctyldiphenylamine, based on the total weight of substituted and unsubstituted diphenylamine in the alkylated diphenylamine composition. This alkylated diphenylamine may also include, at least in some instances, no more than 40 wt. % monosubstituted diphenylamines, based on the total weight of substituted and unsubstituted diphenylamine in the alkylated diphenylamine composition.

Yet another embodiment of the invention is a method of manufacturing a lubricating fluid composition. In this method, an alkylated diphenylamine composition is made as described above and then combined with a lubricant to form the lubricating fluid composition.

DETAILED DESCRIPTION OF THE PREFERRED EMBODIMENT

The present invention is believed to be applicable to methods of forming alkylated diphenylamine compositions and the compositions formed thereby. In particular, the present invention is directed to methods of forming alkylated diphenylamine compositions by the reaction of a) unsubstituted diphenylamine with b) diisobutylene and/or at least one α-olefin having the formula (I)

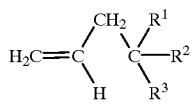

(I)

where $R^1$, $R^2$, and $R^3$ are functional groups that do not substantially interfere with alkylation of unsubstituted diphenylamine via the α-olefinic bond of the α-olefin, and c) a second olefin composition, including at least one second olefin which is more reactive with unsubstituted diphenylamine than diisobutylene and/or the α-olefins of formula (I). The reactions occur in the presence of d) a clay catalyst. The result of this reaction or reactions is an alkylated diphenylamine composition with no more than 3 wt. % unsubstituted diphenylamine, based on the total weight of substituted and unsubstituted diphenylamine in the composition. While the present invention is not so limited, an appreciation of various aspects of the invention will be gained through a discussion provided below.

Reference herein to the weight percentage of any substituted or unsubstituted diphenylamine(s) in a composition is always, unless otherwise specified, based on the total weight of unsubstituted and substituted diphenylamine in that composition (for example, in an alkylated diphenylamine composition or a reaction composition).

The Alkylation Reaction

It is believed that the alkylation reaction of a) unsubstituted diphenylamine with b) diisobutylene and/or one or more α-olefins of formula (I) and c) the second olefin composition in the presence of d) a clay catalyst is or is similar to a Friedel-Crafts alkylation reaction. The reactions are believed to be, at least in part, α-olefinic alkylation reactions in which the α-olefinic functional group of diisobutylene, the α-olefins of formula (I), and/or the second olefins of the second olefin composition alkylates a benzene ring of diphenylamine.

Typically, the second olefin composition includes at least one second olefin that is more reactive with unsubstituted diphenylamine than diisobutylene or the α-olefins of formula (I) under the reaction conditions. As used herein, a first reactant is "more reactive" to unsubstituted diphenylamine than a second reactant if the first reactant reacts more quickly (e.g., has higher activity) with unsubstituted diphenylamine than a second reactant under the same reaction conditions. Reasons for higher activity of one olefin relative to another in this type of chemical reaction include, for example, less steric hindrance, the ability of an olefin to form a more stable carbocation (e.g., a tertiary carbocation as opposed to a secondary carbocation), and/or stabilization of a carbocation formed by an olefin due to other portions of the compound (e.g., benzene rings conjugated with the double bond of the olefin).

Suitable second olefins that are typically more reactive with unsubstituted diphenylamine than diisobutylene and/or the α-olefins of formula (I) include, for example, isobutylene, styrene, and α-methylstyrene. It is believed that isobutylene is more reactive with unsubstituted diphenylamine than diisobutylene for at least steric reasons and that isobutylene is more reactive with unsubstituted diphenylamine than the α-olefins of formula (I) because isobutylene can form a tertiary carbocation which is typically more stable than the secondary carbocation that can be formed by the α-olefins of formula (I). It is believed that styrene and α-methylstyrene are typically more reactive with unsubstituted diphenylamine than diisobutylene and the α-olefins of formula (I) because of the stabilizing effect of the benzene ring conjugated with the double bond.

Components of the Reaction

The unsubstituted diphenylamine or solution of unsubstituted diphenylamine used as a reactant typically contains only low amounts of mono-, di-, or polysubstituted (e.g., alkylated) diphenylamine prior to the alkylation reaction (for example, less than 10 or 20 wt. % based on the total weight of unsubstituted, mono-, di-, and polysubstituted diphenylamines). Preferably, the initial unsubstituted diphenylamine used as a reactant is essentially free (defined as less than 5 wt. % and, usually, less than 2 wt. %) of these mono-, di-, or polysubstituted diphenylamine components.

Diisobutylene and/or the α-olefins of formula (I) are provided in the reaction to alkylate at least one of the benzene rings of unsubstituted diphenylamine. Diisobutylene can be prepared from isobutylene. This product may be a mixture of two isomers: 2,4,4-trimethyl-1-pentene and 2,4,4-trimethyl-2-pentene. The first isomer is an α-olefin and is typically more reactive than the other isomer in the alkylation reaction. In at least some instances, the majority of the diisobutylene, and typically at least 60 wt. % of the diisobutylene, is the first isomer (2,4,4-trimethyl-1-pentene). One commercial source of suitable diisobutylene is Neochem Corp., Bayonne, N.J.

Suitable α-olefins for use in forming alkylated diphenylamine compositions include compounds having the chemical formula:

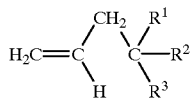

(I)

where $R^1$, $R^2$, and $R^3$ are functional groups that do not substantially interfere with alkylation of unsubstituted diphenylamine by the α-olefinic bond of the α-olefin. The functional groups $R^1$, $R^2$, $R^3$ do not substantially interfere with alkylation of the unsubstituted diphenylamine if, for example, at least 90 mole percent, typically, at least 95 mole percent, and, often, at least 99 mole percent, of the alkylated diphenylamine composition is formed by alkylation of unsubstituted diphenylamine via the α-olefinic bond of the α-olefin.

The α-olefins of formula (I) can typically form secondary carbocations. Suitable α-olefins of formula (I) include, but are not limited to, compounds having 6 to 18 carbon atoms. Among these compounds are linear α-olefins, such as 1-octene, 1-decene, 1-dodecene, 1-tetradecene, 1-hexadecene, and 1-octadecene.

Examples of suitable functional groups for $R^1$, $R^2$, and $R^3$ include hydrogen, alkyl, alkoxy, ester, cyano, and aryl groups. Other functional groups, such as alkenyl groups and substituted alkyl and aryl groups, can be used if these functional groups do not substantially interfere with alkylation of the unsubstituted diphenylamine by the α-olefinic bond between the first carbons, as illustrated in Formula (I). Preferably, the α-olefins of formula (I) have only a single carbon-carbon double bond.

Suitable clay catalysts are aluminosilicates. The aluminum III cations of the clay catalysts are typically bonded in an octahedral arrangement to oxygen anions. Repetition of these $AlO_6$ units in two dimensions form an octahedral layer. Likewise a tetrahedral layer is formed from $SiO_4$ silicate units. Clays are classified according to the relative number of tetrahedral and octahedral layers. Montmorillonite clays, which have been used in organic chemical applications, have an octahedral layer sandwiched between two tetrahedral layers.

The clays useful in the alkylation reaction of unsubstituted diphenylamine include, but are not limited to, those used for bleaching oils and waxes. These are often referred to as acid activated clays. Examples of suitable clays include sub-bentonites or bentonites which are characterized by rapid slaking when in an air dried state and only a slight swelling when placed in water. These clays include the clay mineral montmorillonite. Powdered clay catalysts are preferred.

Suitable commercially available clay catalysts include Filtrol™ and Retrol™ available from Engelhard Corp. (Iselin, N.J.) and Fulcat™ 14, Fulmont™ 700 C., Fulmont™ 237, and Fulcat™ 22B available from Laporte Inc. (Gonzales, Tex.). These clays may include acid activated or acid leached clays, however, acid activated clays are typically preferred. The clay catalysts may contain some water. Removal of the water prior to use may result in lighter colored reaction products. Therefore, it may be desirable to use a low water content clay or to remove the water by heating the clay, optionally, with a nitrogen sweep or with vacuum stripping.

Clay (e.g. acid activated bentonite clay) when used as a catalyst for alkylating unsubstituted diphenylamine typically results in proportionally more monoalkylated diphenylamine than other alkylation catalysts such as $AlCl_3$, $BF_3$, $Et_2O$, and $SbCl_3$. Clay usually results in a lower degree of yellow color in the alkylated product than other alkylation catalysts because clay preferentially absorbs colored species.

When any particular olefin described above is used and the other reaction conditions are optimized the amount of desirable monoalkylated diphenylamine can be substantial and the amounts of less desirable unsubstituted diphenylamine and symmetrically disubstituted diphenylamine (e.g., dioctyl- or dibutyldiphenylamine) can be kept low. These desirable percentages of products are a result of the clay catalyst preferentially catalyzing the alkylation reaction of the unsubstituted diphenylamine rather than the further alkylation of monoalkyldiphenylamine. The tetrahedral and octahedral layers of clay are believed to offer less access to the monoalkyldiphenylamine molecule with its bulky tertiary octyl groups than the unsubstituted diphenylamine molecule to the reactive sites in the catalysts. The monoalkylated diphenylamine is converted to dialkylated or polyalkylated diphenylamine at a slower rate with clay catalyst than with other catalysts allowing the concentration of monoalkylated diphenylamine to increase in the reaction product. By specifying clay catalyst the use of amounts of $AlCl_3$, $ZnCl_3$, $SnCl_4$, $H_3PO_4$, $BF_3$, or other alkylation catalysts is restricted to those amounts that would be effective to alkylate 10 mole percent or less of the unsubstituted diphenylamine under the conditions specified.

The second olefin composition typically includes at least one second olefin that is more reactive with unsubstituted diphenylamine than diisobutylene and/or α-olefins of formula (I). The second olefin composition is typically provided to scavenge or reduce the amount of unsubstituted diphenylamine. Suitable second olefins include, but are not limited to, isobutylene, styrene, and α-methylstyrene.

Although solvents have been used in alkylation reactions to solvate components of the reaction, it is preferred to alkylate diphenylamine with little solvent (e.g. less than 5 wt. % solvent based on the reactive composition of unsubstituted diphenylamine, diisobutylene and/or α-olefin of formula (I), and clay) or no solvent at all. If solvent is used, suitable solvents include, for example, mineral spirits, toluene, and heptane.

Reaction Conditions

Typically, the unsubstituted diphenylamine, diisobutylene and/or α-olefin(s) of formula (I), and clay catalyst are combined together to form a reaction composition. At least a portion of the second olefin composition is added into the reaction composition immediately after forming the reaction composition or a short period of time later (e.g., after or during the time needed to heat the reaction composition to an initial set point temperature in the range of 105 to 200° C.) In contrast to the method described in U.S. Pat. No. 5,750,787, there is no need to wait, before beginning the addition of the second olefin composition for the reaction composition, to include at least 50 wt. % monoalkylated diphenylamine (e.g., monooctyldiphenylamine), based on the total weight of substituted and unsubstituted diphenylamine in the reaction composition.

For the alkylation reaction of unsubstituted diphenylamine with diisobutylene in the presence of clay, the mole ratio of the initial reactants (i.e., diisobutylene:unsubstituted diphenylamine) is typically at least about 0.6:1 to provide sufficient diisobutylene to alkylate a majority of the unsubstituted diphenylamine. The mole ratio of diisobutylene:unsubstituted diphenylamine is typically 2:1 or less to restrain the formation of dioctyldiphenylamine. Suitable mole ratios of the initial reactants are found to be in the range of 0.7:1 to 1.7:1. Typically, the mole ratio of the initial reactants is in the range of, for example, 0.8:1 to 1.4:1.

For α-olefins of formula (I), the mole ratio of the reactants (α-olefins of formula (I):unsubstituted diphenylamine) is typically at least 1:1. In addition, the mole ratio of α-olefins of formula(I):unsubstituted diphenylamine is typically 2:1 or less to reduce the formation of symmetrically disubstituted diphenylamines. Suitable mole ratios of reactants are in the range of, for example, 1.1:1 to 1.7:1. Typically, the mole ratio of these reactants is in the range of 1.2:1 to 1.5:1.

The addition of diisobutylene and/or α-olefins of formula (I) to the alkylation reaction may be metered (e.g., added at a constant or varying rate), added as a single amount or in multiple batches, or by another addition method. The alkylated diphenylamine compositions are typically formed in batches, but the methods described herein can also be used in continuous processes.

The amount of clay catalyst added to the reaction may depend on a variety of factors, including, for example, the desired reaction rate, the difficulty in removing the catalyst from the reaction product, and the desired reaction composition. The clay catalyst is used in alkylation reactions in amounts starting from, for example, about 0.5 wt. %, based on the amount of unsubstituted diphenylamine used as a reactant, and may be up to about 60 wt. %, based on the amount of unsubstituted diphenylamine reactant. Typically, the amount of clay is in the range of about 0.5 wt. % to about 20 wt. %, based on the amount of unsubstituted diphenylamine used as a reactant. In at least some embodiments, the amount of clay is in the range of about 1 wt. % to about 5 wt. %, based upon the amount of unsubstituted diphenylamine used as a reactant.

The initial set point temperature is defined as the initial temperature to which a reaction vessel is initially heated after the unsubstituted diphenylamine and diisobutylene and/or α-olefin(s) of formula (I) are combined, although the reaction of these compounds may occur at lower temperatures. Typically, this initial set point temperature is selected in view of factors such as, for example, the specific reactants, reaction rate, reaction time, and/or reaction composition. It will be understood, however, that, during the reaction, the temperature of the reaction composition may increase above or decrease below the initial set point temperature.

When the alkylation olefin is diisobutylene (DIB), the initial set point temperature is typically at least about 105° C., otherwise the reaction rate may be undesirably slow. The initial set point temperature is typically 200° C. or less to prevent degradation of the reaction products. Typically, the initial set point temperature is within the range of 120° C. to 185° C. Because cracking of octyl groups begins to occur at temperatures above about 165° C., however, the initial set point temperature may be 165° C. or less. Thus, the initial set point temperature may be in the range of 120° C. to 165° C. An initial set point temperature in the range of 145° C. to 165° C. is illustrated in the Examples.

The total reaction time (including the reaction with the second olefin composition) may depend on the reaction temperature. For initial set point temperatures of no more than about 165° C., the total reaction time to end product (including reaction with the second olefin composition) is typically about 1 hour or more and often about 2 to 5 hours. For higher temperatures, the reaction time may be less.

When the alkylation olefin is an α-olefin of formula (I), the initial set point temperature is, for example, at least about 130° C. and may be as high as about 200° C. The reaction time to end product is typically at least one hour and may range from 2 to 10 hours. If a mixture of diisobutylene and α-olefin is used, the initial set point temperature is typically in the range of 130° C. to 200° C.

In some embodiments, the second olefin composition may be added to the unsubstituted diphenylamine and diisobutylene (and/or α-olefin(s) of formula (I)) immediately after combination of these reactants in a reactor or other vessel. In other embodiments, the second olefin composition is added later. For example, in some instances, the unsubstituted diphenylamine is heated in a reaction vessel to an initial set point temperature of at least 105° C. and as high as 200 ° C. Typically, the initial set point temperature is in a range of 120° C. to 165° C. Diisobutylene (and/or α-olefins of formula (I)) are initially at a lower temperature (e.g., room temperature) when added, thereby decreasing the temperature of the reaction mixture. The unsubstituted diphenylamine and diisobutylene (and/or α-olefin(s) of formula (I)) may then be heated to the initial set point temperature. At least a portion of the second olefin is added as the reaction mixture is heated to the initial set point temperature and/or when the reaction mixture reaches the initial set point temperature.

The amount of time to reach the initial set point temperature is, at least in some instances, no more than about 30 minutes. In the Examples, the amount of time to reach the initial set point temperature was no more than 10 minutes. At least a portion of the second olefin is added before reaching the reaction temperature or within 1 to 5 minutes after reaching the initial set point temperature. For reaction temperatures greater than about 165° C., these time periods may be even shorter. Typically, the reaction mixture contains less than 50 wt. % monoalkylated diphenylamine, based on the total weight of unsubstituted and substituted diphenylamine in the reaction mixture, before at least a portion of the second olefin is added. The amount of monoalkylated diphenylamine can be determined by methods such as, for example, liquid or gas chromatography.

The mole ratio of the second olefin composition to unsubstituted diphenylamine used as a reactant is typically at least 0.2:1 and can be as high as 1.7:1. The mole ratio of the second olefin composition to unsubstituted diphenylamine used as a reactant may depend on factors such as, for example, the mole ratio of diisobutylene and/or α-olefins of formula (I) to unsubstituted diphenylamine used in the initial reaction, the desired alkylated diphenylamine composition, and the time at which the second olefin is added. A typical range of mole ratios of second olefin composition:unsubstituted diphenylamine is about 0.5:1 to 1:1. The second olefin may be metered (e.g., added at a constant or varying rate) into the reaction mixture, added as a single amount or in multiple batches, or by another addition method. After addition of the second olefin, the reaction is typically allowed to proceed for at least 1 hour; usually, for two or more hours (for example, for a period ranging from 2 to 5 hours).

In at least some instances, the reaction between the second olefin and unsubstituted diphenylamine is exothermic and, therefore, the reaction temperature may increase above the initial set point temperature with addition of the second olefin. Cooling devices may be used to cool the reaction mixture. In some instances, the temperature of the reaction mixture may have excursions above, for example, 200° C. In some instances, the set point temperature may be increased or decreased prior to or after adding the second olefin composition.

In addition to temperature, the pressure in the reaction vessel may be monitored and, in some instances, controlled.

In those instances, the pressure is typically maintained at 100 psi (about 7×10⁵ Pa) or less. The alkylation reaction can be carried out in an autoclave if high pressures due to the vapor pressure of the olefin are anticipated.

The final alkylated diphenylamine composition is typically a liquid or oil. The alkylated diphenylamine composition typically contains no more than 3 wt. %, and preferably no more than 2 wt. %. unsubstituted diphenylamine, based on the total weight of substituted and unsubstituted diphenylamine in the alkylated diphenylamine composition. For some embodiments, the alkylated diphenylamine composition contains no more than 1 wt. % unsubstituted diphenylamine, based on the total weight of substituted and unsubstituted diphenylamine in the alkylated diphenylamine composition.

When diisobutylene is used as a reactant, the alkylated diphenylamine composition typically contains no more than 25 wt. %, and preferably no more than 20 wt. %, dioctyldiphenylamine, based on the total weight of substituted and unsubstituted diphenylamine in the alkylated diphenylamine composition.

In some embodiments, when isobutylene is the second olefin, the alkylated diphenylamine composition contains no more than 20 wt. %, and preferably no more than 15 wt. %, dibutyldiphenylamine, based on the total weight of substituted and unsubstituted diphenylamine in the alkylated diphenylamine composition.

In some embodiments, when isobutylene is the second olefin, the alkylated diphenylamine composition contains at least 25 wt. %, and preferably at least 30 wt. %, butyloctyldiphenylamine, based on the total weight of substituted and unsubstituted diphenylamine in the alkylated diphenylamine composition.

In at least some instances, the alkylated diphenylamine composition contains no more than 35 wt. % or 40 wt. % monosubstituted diphenylamines, based on the total weight of substituted and unsubstituted diphenylamine in the alkylated diphenylamine composition.

Unreacted olefins may be removed from the reaction product by distillation. This is typically done to remove unreacted olefin contaminants from the alkylated diphenylamine composition. The clay can be removed by filtration or other known separation methods. In some instances, for example, if the amount of diphenylamine is still too high for the particular application, a portion of the remaining unsubstituted diphenylamine may be removed by processes such as fractional distillation or vacuum distillation, if necessary.

The alkylated diphenylamine compositions of this disclosure are useful as antioxidants to stabilize natural source and synthetic source oils and polymers from oxidative degradation during processing reactions and in their final use as lubricants or articles. They may be used in combination with other antioxidants and additives. For example, lubricating fluids usually contain at least 0.2 wt. % antioxidants, based on the total weight of the lubricating fluid, to provide sufficient protection from oxidation. The amount of antioxidant is often no more than about 2 wt. %, based on the total weight of the lubricating fluid. Typically, the amount of antioxidant, such as the alkylated diphenylamine compositions described above, is in the range of 0.5 to 1 wt. % of the total weight of the lubricating fluid. The antioxidant may be any of the alkylated diphenylamine compositions described above.

The lubricating fluids are typically based on a lubricant such as motor, engine, turbine, or other lubricating oils and lubricating greases. The lubricating fluids may include other additives, such as, for example, friction modifiers, detergents, viscosity improvers, corrosion inhibitors, and other antioxidants. The use and types of these additives are known. Examples of suitable detergents include metal sulphonates and metal phenates. Examples of suitable viscosity improvers include polymers, such as polymethacrylates, polyacrylates, polybutenes, and polyvinyl pyrrolidones. Examples of suitable corrosion inhibitors include alkylated benzotriazoles. Examples of other antioxidants are hindered phenols.

EXAMPLES

Example 1

3080 pounds (about 1400 kg) of diphenylamine (Aristech Chemical Corp., Pittsburgh, Pa.) and 125 pounds (about 56.8 kg) of Retrol™ F-20 clay (Engelhard Corp., Iselin, N.J.) were mixed in a reactor and heated to 140° C. for 10 minutes to drive off moisture. These components were then heated to 150° C. About 2658 pounds (443 gallons, about 1208 kg, about 1677 L) of diisobutylene (Neochem, Bayonne, N.J.) at room temperature was then added to the reactor at a rate of 50 gallons (about 189 L) per minute. The reaction temperature dropped and then climbed back to an initial set point temperature of 150° C. Within about 10 minutes of first adding the diisobutylene, 630 pounds (about 286 kg) of isobutylene (Exxon Chemical Co., Baytown, Tex.) was charged in the reactor at a rate of 18 pounds (about 8.2 kg) per minute. Based on experience and Examples illustrated in U.S. Pat. No. 5,750,787, it is believed that the initiation of the addition of isobutylene occurred before the reactive composition of diisobutylene and diphenylamine formed at least 50 wt. % monooctyldiphenylamine.

The reaction continued for 30 minutes after the addition. The temperature reached a maximum of about 200° C. due to the exothermic nature of the reaction. The pressure reached about 80 psi (about 5.5×10⁵ Pa). Cooling water around the reaction vessel was used to maintain the temperature between about 170 to 200° C. The reaction mixture was cooled to 160° C. and 26 pounds (about 11.8 kg) of isobutylene were charged into the reactor at 6 pounds (about 2.7 kg) per minute. The reaction mixture was then allowed to react for an additional 2 hours at 160° C. After completion of the reaction, unreacted diisobutylene was removed at 130° C. and 50 mmHg pressure for 30 minutes. The resulting product was filtered to remove the clay.

The alkylated diphenylamine reaction product was a pale yellow oil with 0.99 wt. % unsubstituted diphenylamine, 14.6 wt. % monobutyldiphenylamine, 21.98 wt. % monooctyldiphenylamine, 9.95 wt. % dibutyldiphenylamine, 27.80 wt. % butyloctyldiphenylamine, and 18.68 wt. % dioctyldiphenylamine as determined by gas chromatography.

Example 2

In a 50 gallon (about 189 L) reactor, 144 pounds (about 65.5 kg) of diphenylamine and 5.9 pounds (about 2.7 kg) of Filtrol™ clay (Engelhard Corp., Iselin, N.J.) were mixed in a reactor and heated to 160° C. for 20 minutes to drive off moisture. About 124.3 pounds (about 56.5 kg) of diisobutylene at room temperature was then added to the reactor over the period of one minute or less. The reaction temperature dropped and then climbed back to an initial set point temperature of 160° C. Within about 10 minutes of first adding the diisobutylene, 28.7 pounds (about 13 kg) of isobutylene was charged in the reactor over a period of about 30 minutes such that the pressure was kept below about 90 psi (about 6.2×10⁵ Pa). Based on experience and Examples illustrated in U.S. Pat. No. 5,750,787, it is believed that the initiation of the addition of isobutylene occurred before the reactive composition of diisobutylene and diphenylamine formed at least 50 wt. % monooctyldiphenylamine.

The reaction continued for 30 minutes after the addition. The temperature during this period reached a maximum of about 170° C. due to the exothermic nature of the reaction. Cooling water around the reaction vessel was used to maintain the temperature at about 170° C. for 30 minutes. The reaction mixture was cooled to 140° C. and 8.6 pounds (about 3.9 kg) of isobutylene were charged into the reactor at about 0.3 pounds (about 0.14 kg) per minute. The reaction mixture was then allowed to react for an additional 2 hours at 140° C. After completion of the reaction, unreacted diisobutylene was removed at 130° C. and 50 mmHg pressure for 30 minutes. The resulting product was filtered to remove the clay.

The alkylated diphenylamine reaction product was a pale yellow oil with 0.9 wt. % unsubstituted diphenylamine, 14.7 wt. % monobutyldiphenylamine, 20.1 wt. % monooctyldiphenylamine, 13.5 wt. % dibutyldiphenylamine, 32.5 wt. % butyloctyldiphenylamine, and 17.3 wt. % dioctyldiphenylamine as determined by gas chromatography.

Example 3

In a 50 gallon (about 189 L) reactor, 144 pounds (about 65.5 kg) of diphenylamine and 5.9 pounds (about 2.7 kg) of Filtrol™ clay (Engelhard Corp., Iselin, N.J.) were mixed in a reactor and heated to 160° C. for 20 minutes to drive off moisture. About 124.3 pounds (about 56.5 kg) of diisobutylene at room temperature was then added to the reactor at a rate of about 60 pounds (about 27 kg) per minute. The reaction temperature dropped to 140° C. and then climbed back to an initial set point temperature of 160° C. Within about 10 minutes of first adding the diisobutylene, 37.4 pounds (about 17 kg) of isobutylene was charged in the reactor over one hour. The temperature during this period reached a maximum of about 190° C. due to the exothermic nature of the reaction. Based on experience and Examples illustrated in U.S. Pat. No. 5,750,787, it is believed that the initiation of the addition of isobutylene occurred before the reactive composition of diisobutylene and diphenylamine formed at least 50 wt. % monooctyldiphenylamine.

The reaction mixture was then allowed to react for an additional 2 hours at 160° C. After completion of the reaction, unreacted diisobutylene was removed at 130° C. and 50 mmHg pressure for 30 minutes. The resulting product was filtered to remove the clay.

The alkylated diphenylamine reaction product was a pale yellow oil with 1.4 wt. % unsubstituted diphenylamine, 17.3 wt. % monobutyldiphenylamine, 21.5 wt. % monooctyldiphenylamine, 12.5 wt. % dibutyldiphenylamine, 34.4 wt. % butyloctyldiphenylamine, and 16.9 wt. % dioctyldiphenylamine as determined by gas chromatography.

Example 4

The same conditions as those described in Example 3 were used except that 43 pounds (about 19.5 kg) of isobutylene was added. Based on experience and Examples illustrated in U.S. Pat. No. 5,750,787, it is believed that the initiation of the addition of isobutylene occurred before the reactive composition of diisobutylene and diphenylamine formed at least 50 wt. % monooctyldiphenylamine. The alkylated diphenylamine reaction product contained less than 0.6 wt. % unsubstituted diphenylamine.

Example 5

The same conditions as those described in Example 3 were used except that, instead of isobutylene, 62 pounds (about 28.2 kg) of styrene (Chevron Chemical Co., San Ramon, Calif.) was charged to the reactor at a temperature of 140° C. over one hour. Based on experience and Examples illustrated in U.S. Pat. No. 5,750,787, it is believed that the initiation of the addition of isobutylene occurred before the reactive composition of diisobutylene and diphenylamine formed at least 50 wt. % monoalkylated diphenylamine. The alkylated diphenylamine reaction product contained less than 2 wt. % unsubstituted diphenylamine and less than 20 wt. % dioctyldiphenylamine.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

What is claimed is:

1. A method of manufacturing an alkylated diphenylamine composition, comprising steps of:

(a) reacting unsubstituted diphenylamine and at least one olefin in the presence of a clay catalyst to form a reactive composition wherein the at least one olefin comprises diisobutylene or α-olefins of the chemical formula (I):

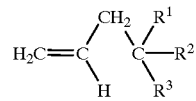

or combinations thereof, wherein $R^1$, $R^2$, and $R^3$, independently, can be hydrogen, alkyl, alkoxy, ester, cyano or aryl groups; and (b) adding a second olefin composition to the reactive composition to react with the reactive composition and generate an alkylated diphenylamine composition comprising no more than 3 wt. % unsubstituted diphenylamine, based on the total weight of unsubstituted and substituted diphenylamine in the alkylated diphenylamine composition, (i) wherein at least a portion of the second olefin composition is added to the reactive composition prior to forming, in the reactive composition, at least 50 wt. % monoalkylated diphenylamine, based on the total weight of unsubstituted and substituted diphenylamine in the reactive composition at the time of initiating addition of the second olefin composition.

2. The method of claim 1, wherein the step of reacting unsubstituted diphenylamine with at least one olefin comprises reacting unsubstituted diphenylamine and diisobutylene in the presence of a clay catalyst to form a reactive composition.

3. The method of claim 2, wherein the step of adding a second olefin composition comprises adding isobutylene to the reactive composition to react with the reactive composition and generate an alkylated diphenylamine composition comprising no more than 3 wt. % unsubstituted diphenylamine and at least 25 wt. % butyloctyldiphenylamine, based on the total weight of unsubstituted and substituted diphenylamine in the alkylated diphenylamine composition.

4. The method of claim 2, wherein the step of reacting unsubstituted diphenylamine and diisobutylene to form a reaction composition comprises heating the reaction composition in a reaction vessel to an initial set point temperature in a range of 140 to 165° C.

5. The method of claim 4, wherein:
   (i) the step of reacting unsubstituted diphenylamine and diisobutylene in the presence of clay catalyst comprises combining the unsubstituted diphenylamine, the diisobutylene, and the clay catalyst in a reaction vessel, and
   (ii) the step of the adding a second olefin composition comprises adding at least a portion of the second olefin composition within 30 minutes of beginning the step of combining the unsubstituted diphenylamine, the diisobutylene, and the clay catalyst in the reaction vessel.

6. The method of claim 1, wherein the step of adding a second olefin composition comprises adding isobutylene.

7. The method of claim 1, wherein the step of adding a second olefin composition comprises adding isobutylene to the reactive composition to react with the reactive composition and generate an alkylated diphenylamine composition comprising no more than 3 wt. % unsubstituted diphenylamine and no more than 40 wt. % monoalkylated diphenylamine, based on the total weight of unsubstituted and substituted diphenylamine in the alkylated diphenylamine composition.

8. The method of claim 1, wherein the step of adding a second olefin composition comprises adding at least one compound of either styrene or α-methylstyrene.

9. The method of claim 1, wherein:
   (i) the step of reacting unsubstituted diphenylamine and at least one olefin in the presence of clay catalyst comprises combining the unsubstituted diphenylamine, the at least one olefin, and the clay catalyst in a reaction vessel, and
   (ii) the step of the adding a second olefin composition comprises adding at least a portion of the second olefin composition within 10 minutes of beginning the step of combining the unsubstituted diphenylamine, the at least one olefin, and the clay catalyst in the reaction vessel.

10. The method of claim 1, wherein reacting unsubstituted diphenylamine and at least one olefin comprises reacting unsubstituted diphenylamine and an α-olefin of formula (I) in the presence of a clay catalyst to form a reactive composition, wherein the α-olefin of formula (I) has 6 to 18 carbon atoms.

11. The method of claim 10, wherein the step of reacting unsubstituted diphenylamine and at least one olefin comprises reacting unsubstituted diphenylamine and an α-olefin of formula (I) in the presence of a clay catalyst to form a reactive composition, wherein $R^1$, $R^2$, and $R^3$ of the α-olefin of formula (I) are independently hydrogen or alkyl.

12. A method of manufacturing an alkylated diphenylamine composition, comprising a step of:
   (a) reacting unsubstituted diphenylamine, diisobutylene, and isobutylene in the presence of a clay catalyst to form an alkylated diphenylamine composition, wherein the alkylated diphenylamine composition comprises at least 25 wt. % butyloctyldiphenylamine, no more than 3 wt. % unsubstituted diphenylamine, and no more than 25 wt. % dioctyldiphenylamine, based on the total weight of unsubstituted and substituted diphenylamine in the alkylated diphenylamine composition.

13. The method of claim 12, wherein the reacting step comprises reacting unsubstituted diphenylamine, diisobutylene, and isobutylene in the presence of a clay catalyst to form an alkylated diphenylamine composition, wherein the alkylated diphenylamine composition comprises at least 30 wt. % butyloctyldiphenylamine, based on the total weight of unsubstituted and substituted diphenylamine in the alkylated diphenylamine composition.

14. The method of claim 12, wherein the reacting step comprises reacting unsubstituted diphenylamine, diisobutylene, and isobutylene in the presence of a clay catalyst to form an alkylated diphenylamine composition, wherein the alkylated diphenylamine composition comprises no more than 40 wt. % monoalkylated diphenylamine, based on the total weight of unsubstituted and substituted diphenylamine in the alkylated diphenylamine composition.

15. The method of claim 12, wherein the reacting step comprises
   (i) combining unsubstituted diphenylamine, diisobutylene, and clay catalyst to form a reaction composition,
   (ii) heating the reaction composition to an initial set point temperature, and
   (iii) adding isobutylene to the reaction composition, wherein at least a portion of the isobutylene is added prior to reaction composition having at least 50 wt. % monooctyldiphenylamine, based on the total weight of substituted and unsubstituted diphenylamine in the reaction composition.

16. The method of claim 15, wherein the heating step comprises heating the reaction composition in a reaction vessel to an initial set point temperature in the range of 140 to 165° C.

17. The method of claim 16, wherein the reacting step comprises
   (i) combining unsubstituted diphenylamine, diisobutylene, and clay catalyst to form a reaction composition, and
   (ii) adding isobutylene to the reaction composition, wherein at least a portion of the isobutylene is added within 30 minutes of beginning the step of combining the unsubstituted diphenylamine, diisobutylene, and clay catalyst.

18. The method of claim 12, wherein the reacting step comprises
   (i) combining unsubstituted diphenylamine, diisobutylene, and clay catalyst to form a reaction composition, and
   (ii) adding isobutylene to the reaction composition, wherein at least a portion of the isobutylene is added within 10 minutes of beginning the step of combining the unsubstituted diphenylamine, diisobutylene, and clay catalyst.

* * * * *